United States Patent [19]

Brown

[11] Patent Number: 4,608,996
[45] Date of Patent: Sep. 2, 1986

[54] EXTERNAL BLOOD PARAMETER DIAGNOSTIC SYSTEM

[75] Inventor: David C. Brown, Miami, Fla.

[73] Assignee: Cordis Corporation, Miami, Fla.

[21] Appl. No.: 639,574

[22] Filed: Aug. 10, 1984

[51] Int. Cl.⁴ .............................................. A61B 5/02
[52] U.S. Cl. .................................. 128/760; 128/748; 128/765; 604/32; 604/118; 604/248
[58] Field of Search ............... 128/748, 765, 637, 760, 128/692; 604/7, 27, 30, 32, 34, 35, 36, 38, 118, 121, 169, 181, 183, 248, 250

[56] References Cited

U.S. PATENT DOCUMENTS

| | | | |
|---|---|---|---|
| 1,238,521 | 8/1917 | Janish | 604/34 X |
| 2,625,932 | 1/1953 | Salisbury | 604/7 |
| 2,646,042 | 7/1953 | Hu | 604/118 X |
| 3,157,201 | 11/1964 | Littmann | 604/32 X |
| 3,185,179 | 5/1965 | Harautuneian | 604/248 X |
| 3,674,012 | 7/1972 | Sage | 128/637 |
| 3,780,736 | 12/1973 | Chen | 604/32 |
| 3,834,372 | 9/1974 | Turney | 604/248 X |
| 3,841,307 | 10/1974 | Friedell | 128/637 |
| 4,083,363 | 4/1978 | Philpot, Jr. | 128/637 |
| 4,476,877 | 10/1984 | Barker | 128/692 X |

Primary Examiner—John F. Niebling
Assistant Examiner—Nam X. Nguyen
Attorney, Agent, or Firm—Yount & Tarolli

[57] ABSTRACT

An externally located blood monitoring system has a single access to a patient's blood vessel for monitoring blood associated parameters. A three-position valve permits three modes of operation including flushing, blood pressure monitoring while maintaining patency of the access, and blood sampling while also permitting monitoring of other blood related parameters, such as blood temperature.

17 Claims, 10 Drawing Figures

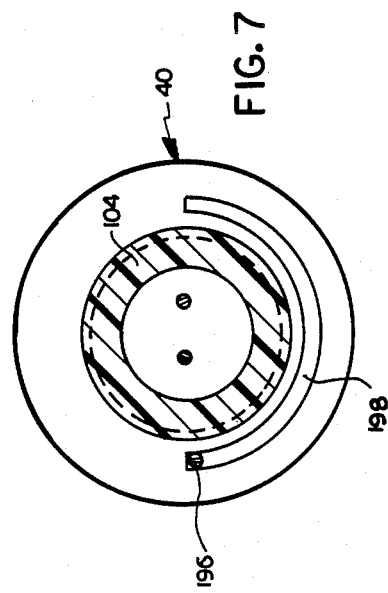
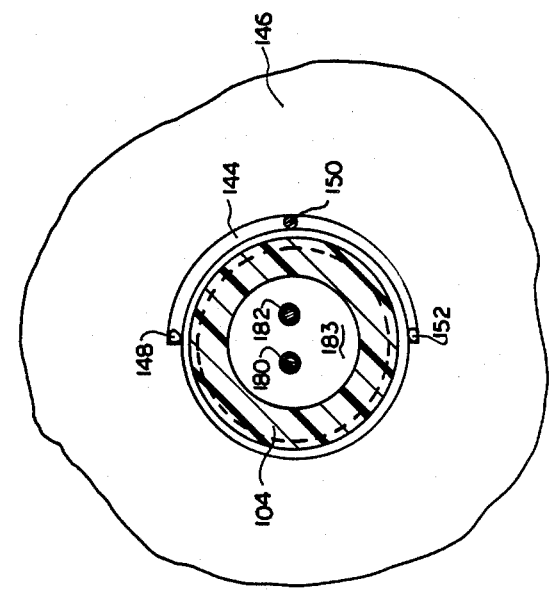
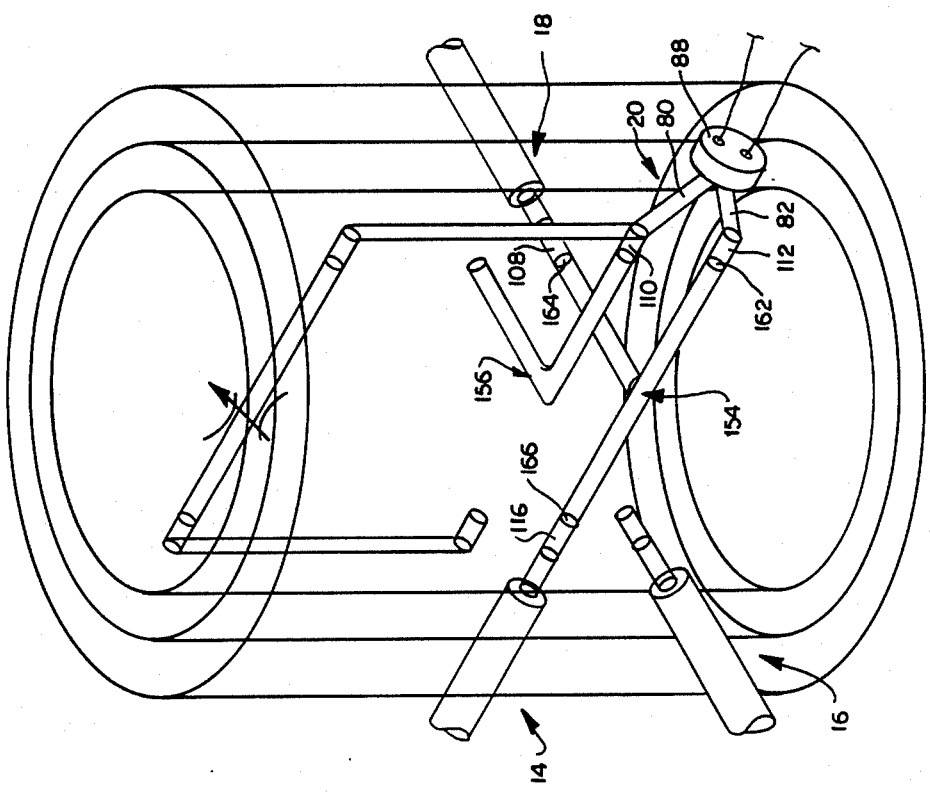

EXTERNAL BLOOD PARAMETER DIAGNOSTIC SYSTEM

BACKGROUND OF THE INVENTION

This invention relates to the art of diagnosing various blood related parameters of a patient with apparatus connected to but located externally of a patient's body.

The invention is particularly applicable in conjunction with analyzing blood related parameters with respect to the vascular system and is described with particular reference thereto, although it is to be appreciated that the invention may be applied in other body systems.

It is known in the art to provide externally located devices for use in monitoring various parameters of blood flowing in the cardiovascular system of a patient. Such devices may, for example, take the form of a single lumen in-dwelling catheter installed in a patient's blood vessel so as to have access to the cardiovascular system. A separate catheter is employed, each having access to a patient's blood vessel, for each blood parameter to be monitored. It is frequently necessary to move the location of each catheter at periodic intervals, such as every 72 hours, and each new location requires a new puncture into the patient's blood vessel. This causes patient discomfort as well as the chances for complications.

It is, therefore, desirable when monitoring several parameters of blood in the cardiovascular system, that a single access to a patient's blood vessel be obtained to accommodate monitoring of all parameters.

The prior art recognizes the desirability of having a single access to a patient's blood vessel, as is evident by U.S. Pat. No. 4,072,146 to Howes. Howes proposes a system wherein a single catheter is inserted into a patient's blood vessel. But the catheter has a plurality of lumens each providing a passageway for conveying fluid; one for obtaining blood samples, another for use communicating with a source of IV fluid and another for use in intraveneous pressure monitoring. While such a system provides a single access, it nevertheless requires a catheter of sufficient diameter to accommodate the three lumens while still being of a size to enter into a patient's blood vessel. This diameter limits the number of parameters that may be monitored to that of the number of lumens within the catheter.

It is desirable to provide a blood monitoring system employing a catheter having but a single lumen and having a single access into a patient's blood vessel while permitting several parameters of blood to be monitored.

Typically, prior art systems involving external devices for measuring blood pressure or obtaining blood samples and the like include a confusing array of lines, valves, various adjustments, and a multitude of couplings which presents the potential for leakage. Such is illustrated, for example, in the aforementioned U.S. Pat. No. 4,072,146 to Howes. Another example, for blood pressure monitoring, is illustrated by the U.S. Pat. No. 4,431,009 to Marino et al.

It is desirable in such a system to employ a single valve actuator for controlling both blood flow and parenteral flow to avoid confusion during operation.

OBJECTS OF THE INVENTION

It is an object of the present invention to provide an externally located blood monitoring system having a single access to a patient's blood vessel for monitoring a plurality of blood associated parameters.

It is a still further object of the present invention to provide such a system wherein parenteral and blood flow are controlled by a single valve actuator.

It is a still further object of the present invention to provide a system employing a plurality of series connected flow through sensors for various parameters leading to a blood sampling port so that blood may be drawn past the sensors during blood sampling, together with a flow-through blood pressure sensor located downstream from the blood sampling port.

It is a still further object of the present invention to provide a system which is relatively inexpensive and sterile permitting multiple tests, such as blood temperature, blood pressure, ph, electrolytes and gases, etc., as well as blood sampling, while having only a single access to the patient's body.

SUMMARY OF THE INVENTION

The above and other objects are achieved in accordance with the present invention employing apparatus for use in externally monitoring various blood related parameters and for obtaining blood samples from a single communication with a patient's blood vessel. The apparatus includes a housing having a patient port for communication with the patient's blood vessel, a blood sampling port for providing blood samples, a parenteral port for communication with a pressurized source of parenteral fluid and a pressure sensor chamber containing a flow through pressure sensor for measuring the pressure of fluid flowing therethrough.

A flow control device is located in the housing for selectively controlling fluid flow between the ports and through the pressure chamber. The control device has three positions. In a first position a fluid flow path is completed from the parenteral port through the pressure sensor and then to the sampling port for flushing operations by the parenteral fluid, while blocking flow to the patient port. In a second position a fluid flow path is completed from the parenteral port through the flow through pressure sensor to the patient port, while blocking the sampling port, for measuring blood pressure. In a third position a fluid flow path is completed from the patient port to the sampling port, while blocking the pressure chamber and the parenteral port, for blood sampling.

In accordance with a more limited aspect of the present invention, a plurality of series connected flow through sensors are connected in series with the patient port so as to be responsive to blood flow therethrough when the flow control device is in its third position.

In accordance with a still further aspect of the present invention, the flow control device takes the form of a single rotary valve actuator for completing the flow paths enumerated above.

Still further in accordance with the present invention, a capillary tube is located in the flow path defined when the actuator is in its second position. The capillary tube is adjustable to vary the flow rate of the parenteral fluid flowing therethrough.

Still further in accordance with the present invention, a push button actuator is provided for by passing the variable flow capillary.

BRIEF DESCRIPTION OF THE DRAWINGS

The foregoing and other objects and advantages of the invention will become more readily apparent from a consideration of the following description taken in conjunction with the accompanying drawings wherein:

FIG. 6 is a sectional view taken along line 6—6 in FIG. 4 looking in the direction of the arrows;

FIG. 7 is a sectional view taken along line 7—7 in FIG. 4 looking in the direction of the arrows;

FIG. 10 is a schematic illustration of the valve operation during blood sampling operations.

DETAILED DESCRIPTION OF PREFERRED EMBODIMENT

Figure 1:
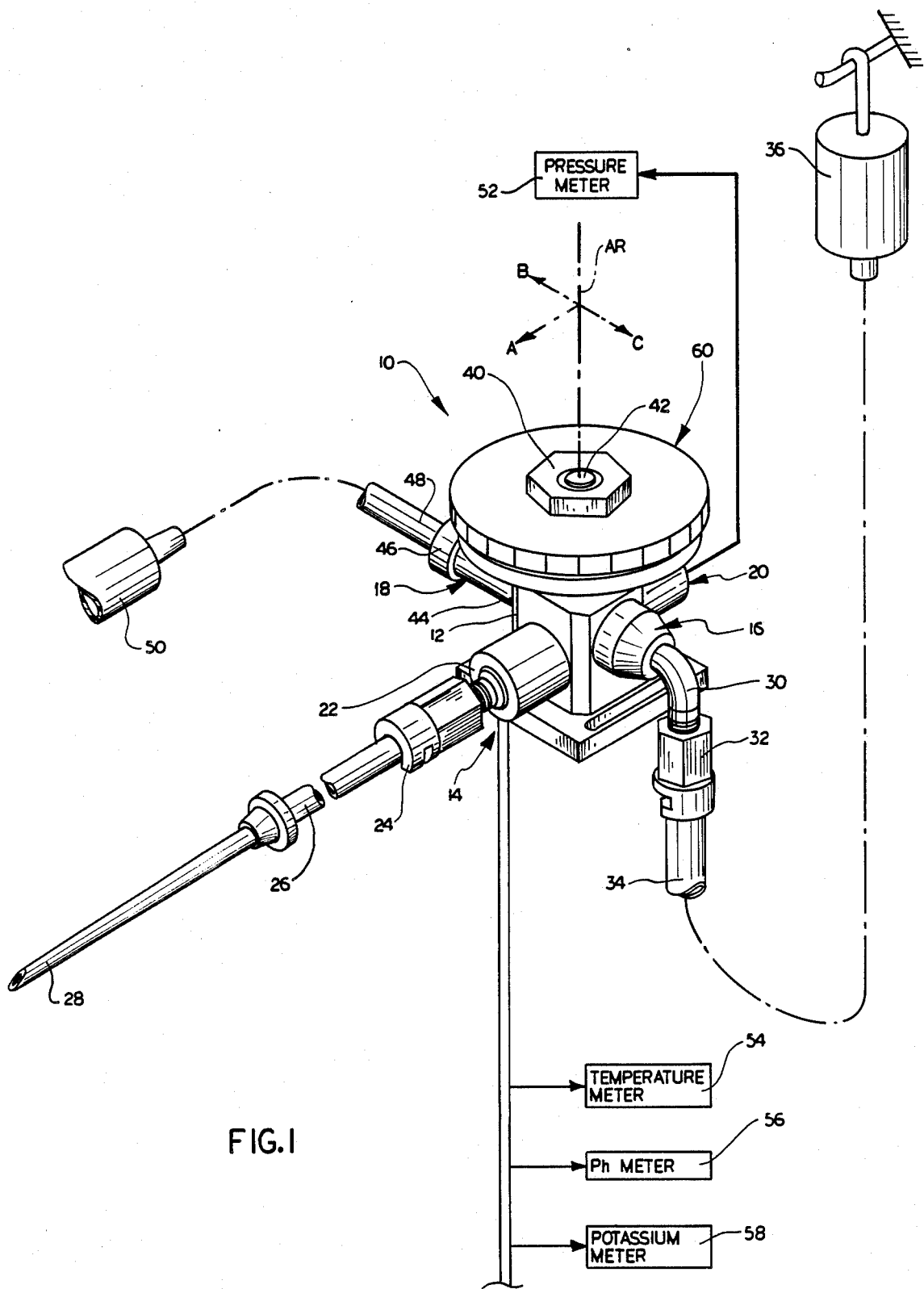
FIG. 1 is a combined perspective-schematic illustration of the preferred embodiment.

Reference is now made to the drawings wherein the showings are for the purposes of illustrating a preferred embodiment of the invention only and not for purposes of limiting same. In FIG. 1 there is illustrated an application of the invention in the form of an external disposable system connected to a patient's blood vessel by way of a standard in-dwelling arterial catheter. This provides a single access and line of communication to the patient for measuring the various blood related parameters including, for example, temperature, ph level, potassium, as well as blood pressure monitoring and blood sampling. The system employs a fluid control device 10 which may be fabricated from a medical grade polycarbonate, and which, for example, may be of a size sufficient to be formed within a cube having dimensions on the order of 5 cm.×5 cm.×5 cm. The construction, as will be brought in detail hereinafter, is sufficiently inexpensive that the flow control device may be considered as being disposable. Hence, the cost for performing tests can be conveniently charged by a hospital on a per patient basis.

The device 10 includes a housing 12 having three ports including a patient port 14, a parenteral port 16 and a blood sampling port 18, as well as integrally formed pressure transducer chamber 20. Each port is fitted with a suitable coupling for connection with a fluid flow line. Thus, the patient port 14 has a tubular threaded extension 22 on which there is threaded a fluid coupling 24 for making fluid tight engagement with a fluid line 26 leading to a standard catheter 28. The catheter 28 may be of any well known single lumen type which may be inserted into a patient's blood vessel leading to the cardiovascular system. This single lumen together with the tubular line 26, then, provides a single line of communication from the patient's blood vessel to the patient port 14 of the flow control device 10.

Port 16 also includes a tubular extension 30 which is threaded about one end and to which there is threaded a coupling 32 for engagement with a fluid line 34. Fluid line 34 communicates with a source of parenteral fluid taking the form of a fluid reservoir 36. The fluid contained in the reservoir 36 is typically a physiologic saline solution (sometimes referred to as I.V. solution). This fluid communicates through flow control device 12 and the catheter 28 to the in-dwelling end thereof within the patient's blood vessel to maintain patency. The fluid is in communication with the blood in the patient's blood vessel and transmits blood pressure variations by way of the flow control device 10 to the pressure chamber 20 for blood pressure monitoring. During pressure monitoring operations, the saline solution is typically maintained at a flow rate on the order of 3.0 ml/hr to 30 ml/hr to maintain patency. This will be discussed hereinafter. The flow control device 10 is operative to transmit the saline solution through a capillary tube which is adjustable by means of a rotary thumb screw 40 to adjust the flow rate from approximately 3.0 ml/hr to 30 ml/hr to accommodate various patient needs. This variable flow capillary can be by-passed by means of a push button 42, which when actuated provides a flow rate on the order of 30 ml/hr.

The third port 18, which serves as a blood sampling port, is provided with a tubular extension 44 which is threaded at one end and which, in turn, is threaded to a suitable coupling 46 for connection with a fluid conveying line 48 in communication with a blood withdrawing syringe 50 or the like.

The pressure chamber 20, as will be described in greater detail hereinafter, contains a flow-through pressure transducer which is operative during the pressure monitoring mode of operation to monitor blood pressure variations transmitted by way of the saline solution. An electrical output taken from the pressure transducer is supplied to a suitable pressure meter 52. Meter 52 may take any suitable form well known in the art, including a visual display as well as a chart recorder and the like. This may provide continuous dynamic pressure measurements including systolic, diastolic, pulse and mean pressure.

The inlet chamber in fluid communication with the patient port 14 contains additional flow-through sensors which preferably are aligned in a series or tandem relationship. Several sensors are contemplated including, for example, a temperature sensor, a ph sensor and a potassium sensor. Each is electrically connected to an output meter of the type indicated above with respect to pressure meter 52. A single multiplexed meter or a plurality of individual meters may be employed. In the case illustrated in FIG. 1, there is a meter for each parameter including a temperature meter 54, a ph meter 56 and a potassium meter 58. It is contemplated that these meters will provide readings of the parameters involved during blood sampling operations while blood is drawn past the sensors into the control device 10 by way of the patient port 14.

The flow control device 10 functions to provide flushing, maintenance of patency, blood sampling (together with monitoring of temperature, ph and potassium) and flow-through pressure measurements. These are accomplished in conjunction with a three-position rotary valve actuator 60 which, as will be described in greater detail hereinafter, rotatably positions a valve body within housing 12 at three different positions. By the operator manually grasping the valve actuator 60, it may be rotatably displaced about its axis of rotation AR to positions A, B, and C as indicated by the arrows in FIG. 1. The rotational distance between positions A-B is 90° and similarly, from B-C is 90°. Each is a detented position so that the operator easily knows when the valve actuator is in its proper location. These positions place the valve body within the housing in locations to complete various flow paths to perform the functions enumerated above.

The valve actuator 60 may be rotated so as to be in position A. This is the flush position and is normally the initial connection to a patient. In this position, the patient port 14 is blocked and a flow path is completed by the valve body within housing 12 for the pressurized parenteral fluid source 36 to be connected for fluid flow through the housing and valve body and through a flow-through pressure sensor in the pressure chamber 20 and, thence, out of the housing through the blood sampling port 18. This operation flushes the system and eliminates trapped air bubbles.

Position B of the rotary actuator 60 is the most commonly utilized in a clinical setting and provides continuous dynamic pressure measurements. In this position, the blood sample port 18 is blocked and a flow path is completed from the pressurized parenteral fluid source 36 into the housing by way of the parenteral port 16 and, thence, through the valve body and a capillary tube and through the flow-through pressure sensor in the pressure chamber 20 and thence through the valve body and the patient port 14 so as to be in communication with the blood flow in the patient's blood vessel.

The capillary flow rate may be adjusted by rotating the capillary adjustment turn screw 40 about its axis of rotation AR through an angle of 180°. The capillary flow rate is adjustable from 3.0 ml/hr to 30 ml/hr to accommodate various patient needs. The adjustable flow rate can be bypassed by depressing push button 42 downwardly in the direction of the axis of rotation AR at which the capillary flow rate will be at its upper level, i.e., on the order of 30 ml/hr.

When the rotary actuation is in position C, the parenteral port 16 is blocked and the patient is connected directly to the sample port 18. In this position a flow path is completed from the patient to the patient port 14 and, thence, through the valve body within housing 12 and exiting from the housing 12 by means of the sample port 18. In this position, a blood sample may be obtained as with syringe 50. Blood may be returned from the sample syringe to the patient without having left a sterile environment.

Figure 2:
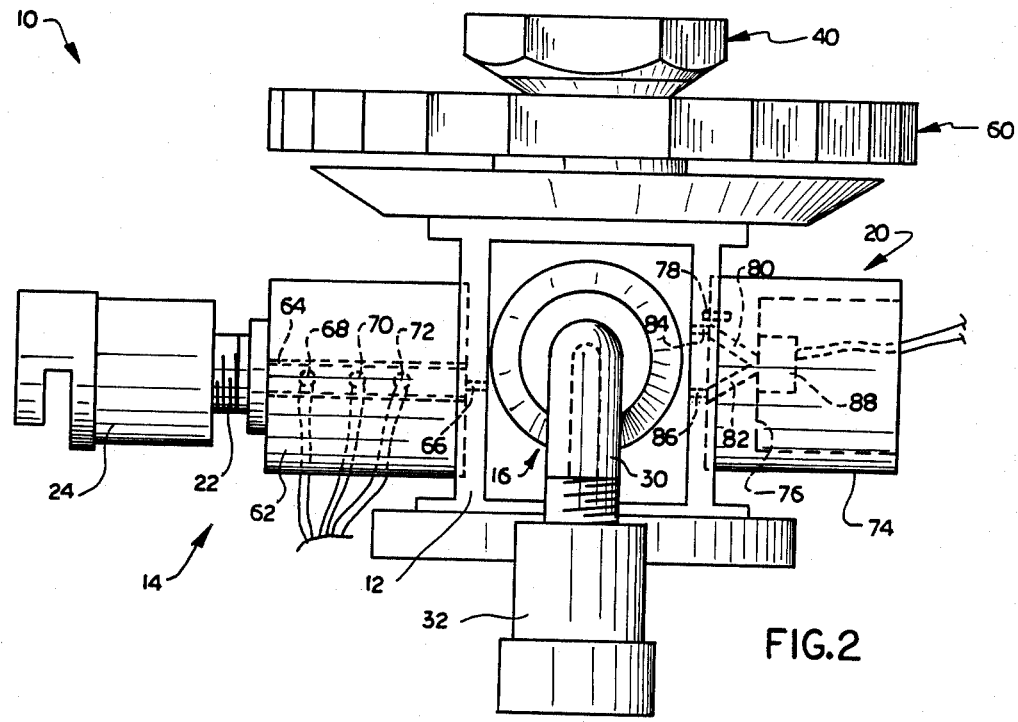
FIG. 2 is an elevational view of the parenteral port side of the fluid control device in FIG. 1.
Figure 3:
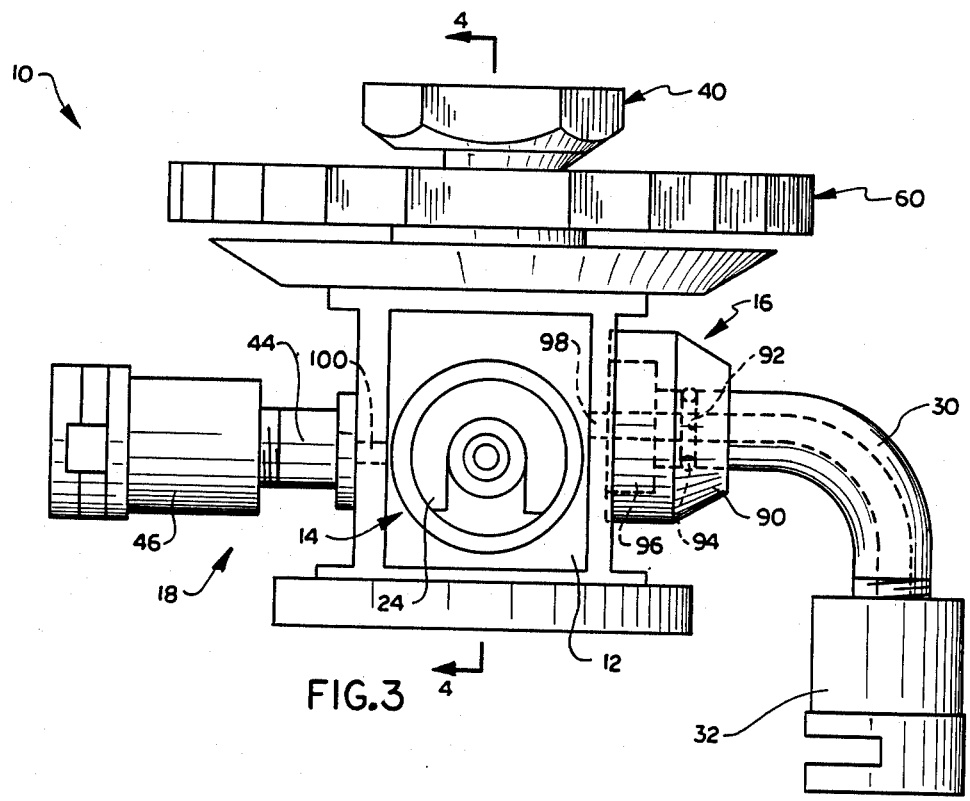
FIG. 3 is an elevational view of the patient port side of the fluid control device in FIG. 1.
Figures 4, 5:
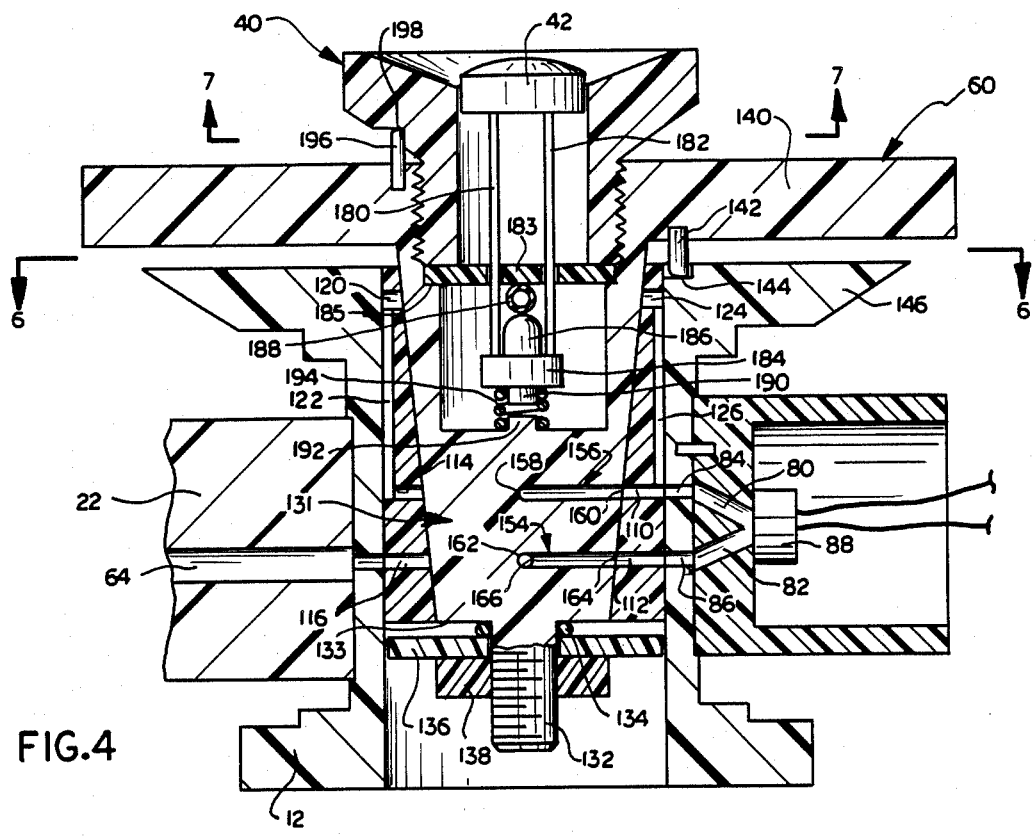
FIG. 4 is a sectional view taken along line 4—4 in FIG. 3 looking in the direction of the arrows.
FIG. 5 is a sectional view as in FIG. 4 but with the rotary actuator displaced clockwise (as viewed in FIG. 1) by 90°.

Having generally described the embodiment of the invention as illustrated in FIG. 1, attention is now directed to the following more detailed description. As seen in FIGS. 2 and 3, the patient port 14 includes a hollow cylindrical inlet chamber 62 extending outwardly from housing 12 and terminating in the tubular extension 22. Within the chamber 62 the tubular extension 22 is in communication with a fluid conveying tube 64 which conveys fluid to the interior of the housing by way of a centrally aligned aperture 66 through the housing 12. Tube 64 and chamber 62 are sufficiently long to accommodate the positioning, within tube 64, of in-line sensors 68, 70 and 72 for respectively measuring temperature, ph level and potassium level of blood flowing through tube 64 during blood sampling operations. Each of the sensors is conventional in the art, and for example, may take the form of a pair of wire leads, together with a beaded thermistor sensor head interconnecting the two wire leads all located within the interior of tube 64. Alternatively, they may take the form of Ion sensitive field effect transistors, or coated wire Ion selective membrane sensors or Ion sensitive glass heads. Similarly, reference sensor half cells may be included. Each sensor, then, has a pair of conductors extending through chamber 62 where the wires may be bundled and insulated from each other as a bus for connection with suitable meters, such as the temperature meter 54, the ph meter 56 and the potassium meter 58.

The pressure transducer chamber 20 is mounted on the pressure side of housing 12 opposite that of the patient port 14. The pressure transducer chamber takes the form of a cylindrical cup-shaped structure turned on its side and having its floor 76 mounted to the housing 12 and located in place by means of a metal pin 78. A pair of vertically spaced apertures 80 and 82 extend through floor 76 so as to be somewhat V-shaped, the apex terminating within the interior of the cup-shaped structure. These apertures 80 and 82 cooperate with apertures 84 and 86, respectively, extending through housing 12 for communication with the valve body therewithin (to be described below). At the apex where apertures 80 and 82 merge, they are in fluid communication with a pressure transducer 88 which serves to provide an electrical output signal representative of the pressure of fluid flowing between these two apertures. Although different forms may be used, preferably a Keller silicone diaphragm type piezoresistive transducer is employed. The diaphragm transducer is positioned so as to be in fluid communication with the fluid flowing between the apertures 80 and 82. The diaphragm operates in conjunction with a wheatstone bridge network so that as the pressure varies, output signals are provided which vary in accordance with pressure. These output signals are supplied by output conductors to a suitable meter, such as the pressure meter 52, in FIG. 1.

Preferably, the operating characteristics of the pressure transducer conform with that set forth below in Table I.

TABLE I

| | |
|---|---|
| Operating pressure range | −50 to +300 mm Hg |
| Sensitivity | 5 micro volts/v/mm Hg ± 1% |
| Excitation voltage | 2.5–10.0 volts DC or RMS AC |
| Volume displacement | less than .001 mm$^3$/100 mm Hg |
| Linearity and hysteresis | less than 1.0% of reading or 1.0 mm Hg whichever is greater |
| Zero output offset range | ±30 mm Hg maximum |
| Leakage current | less than 10 micro-amps RMS at 115 volts RMS AC |
| Defibrillation withstand | 5 repeated discharges within 5 minutes of 400 joules delivered across 50 ohm load |
| Natural frequency-transducer | greater than 100 Hz in air |
| Sensitivity drift with temperature | 0.1%/°C. |
| Zero drift with temperature | 0.3 mm Hg/°C. |
| Zero drift with time | 1.0 mm Hg/8 hours |
| Overpressure withstand | −700 to +400 mm Hg (over pressure relief at 2000 mm Hg) |
| Operating temperature range | 10° C. to 45° C. |
| Shock-transducer | Withstands three falls from height of one meter onto concrete floor |
| Storage temperature range | −35° C. to 60° C. |
| Operating life-transducer | greater than 500 hours |

The parenteral fluid port 16 includes a hollow cylindrical fitting 90 which is tapered at one end and which receives one end of extension 30. To this end, extension 30 has an annular groove 92 which cooperates with a similar annular groove within fitting 90 and the parts are held together with an O-ring 94 to permit the extension 30 to be swivelled about an axis of rotation extending through the O-ring while maintaining a fluid tight seal. Fitting 90 has an enlarged chamber 96 facing the housing 12 and which receives a radial flange 96 of extension 30 and which holds the extension in place in the fitting 90.

On the blood sampling port side, extension 44 is secured at one end to housing 12 and is in fluid communication with the interior of the housing by way of an aperture 100.

A vertically extending cylindrical bore extends through housing 12 coaxially about the axis of rotation AR. The upper portion of this bore is fitted with a valve sleeve 104 which is tapered inwardly from the top to the bottom of the sleeve. This sleeve is provided with apertures which are in alignment with the apertures in the housing 12 for fluid communication. Sleeve 104 has an aperture 106 which, when the sleeve is in assembly within housing 12, is in alignment with aperture 98 in housing 12 and which leads to the parenteral fluid port 16. Diametrically opposite aperture 106, but at a slightly lower level, there is provided a second aperture 108 which is in alignment with aperture 100 in housing 12 and which leads to the sampling port 18. On the pressure side of sleeve 104 there is a pair of vertically spaced apertures 110 and 112 which are in registry with apertures 84 and 86, respectively, which lead to the pressure chamber. On the patient side of sleeve 104, there is also provided a pair of vertically spaced apertures 114 and 116. Aperture 116 is in registry with aperture 66 in housing 12 leading to the patient port 14. Spaced vertically above aperture 114 there is provided an additional aperture 120. A vertically extending groove 122 in the outside wall of sleeve 104 connects apertures 114 and 120. Similarly, another aperture 124 in sleeve 104 is vertically spaced from aperture 110 and these two apertures are interconnected by a vertically extending groove 126 in the outside wall of sleeve 104. The purpose of these apertures and grooves will become more readily apparent from the following description in conjunction with the valve body.

The rotary actuator 60 serves to rotatably drive a valve body 130 about the axis of rotation AR (FIG. 1). The valve body and the rotary actuator are a single unitary part of molded plastic. The valve body 130 is tapered inwardly over its length so as to fit the inner tapered wall of valve sleeve 104 in which the valve body is located during operation. Extending downwardly from the lower portion of the valve body there is provided a threaded shaft 132. In assembly, this extends beyond sleeve 104. An O-ring 134 surrounds shaft 132 and is brought up into abutment against the bottom surface 133 of the valve body. A washer 136 is also carried by the threaded shaft and is fitted against the O-ring 134 and this assembly is held in place by a nut 138 threaded to the shaft 132. This holds the valve body in place within housing 12 while permitting rotation of the valve body about its axis of rotation AR.

The valve actuator 60 takes the form of a radially extending flange 140 which extends outwardly from the upper portion of the valve body 130. On its lower side, the flange 140 carries a stop pin 142 which extends downwardly and during operation this rides in an arcuate groove 144 located in the upper surface of a radially extending flange 146 which extends outwardly from the upper portion of the housing 12. Flange 146 is provided with detents 148, 150 and 152 in the groove 144. Detents 148 and 152 define the limits of rotation of the rotary actuator 60. Detent 150 defines an intermediate position. These detents help the operator in positioning the rotary actuator from positions A to B to C discussed hereinbefore with reference to FIG. 1 as the rotor is being rotated about its axis of rotation AR. This, then, defines a total arcuate length of 180°.

The lower portion 131 of the valve body 130 is essentially solid with the exception of two passageways extending therethrough. These passageways include a lower T-shaped passageway 154 and an upper L-shaped passageway 156. These passageways cooperate with the apertures in the valve sleeve 104 as well as those through the housing 12 to achieve fluid communication in accordance with those required in valve positions A, B and C. These two passageways 154 and 156 are located in horizontal planes vertically spaced from each other within the lower portion 131 of the valve body. The right angled or L-shaped passageway 156 is defined by two legs oriented at 90° to each other and which make a right angle at a point located at the center of the valve body through which the axis of rotation AR extends. This passageway extends between exterior openings 158 and 160 and which, depending on the angle of rotation of the valve body, cooperate in the detented positions with apertures 106, 110 and 114 in the valve sleeve 104. Similarly the T-shaped passageway 154 is defined by three legs which merge within the valve body at a point coincident with the axis of rotation of the valve body and these legs have exterior openings 162, 164 and 166. These openings cooperate during operation in positions A, B and C with apertures 108, 112 and 116 in the valve sleeve 104.

The upper portion of the valve body 130 is hollowed out so as to provide a cylindrical chamber 168 having a floor 170. Chamber 168 serves to receive a downwardly depending plunger portion of the turn screw 40. The turn screw 40 has a depending cylindrical sleeve portion 172 and which extends into chamber 168 in the valve body. The sleeve portion is threaded about its outside diameter with the threading cooperating with corresponding threading on the inside diameter of chamber 168. This permits the turn screw 40 to be threaded into and threaded out of chamber 168 by rotating the thumb screw about its axis of rotation AR.

The thumb screw 40 is provided with a cylindrical bore 174 coaxial with the axis of rotation AR. This bore serves to slidably receive push button 42. This push button has an upper curved surface which extends slightly above bore 174 so as to be accessible to an operator desiring to press downwardly on the push button. A pair of spaced apart rods 180 and 182 are secured to the bottom surface of push button 42 and which extend downwardly and are fixed to a support plate 184 which in turn carries an upwardly extending cam 186. In the space above cam 186 but below the bottom of push button 42, there extends a resilient plastic tubing which serves as a capillary tube 188. A stub shaft 190 extends downwardly from plate 184 and is in registry with an upstanding support stub 192 extending upwardly from the floor 170 of chamber 168. A coil spring 194 is carried by the stub shafts 190, 192 so as to resiliently bias plate 184 and hence cam 186 upwardly against tube 188.

Rods 180 and 182 extend through a disc plate 183 which, in operation, rests on a radial flange 185 when pressed downward by the bottom of sleeve portion 172, when screwed all the way down. The bottom surface of plate 183 then rests on the upper side of capillary tube 188, without deflecting the tube. This permits a high rate of fluid flow, on the order of 3.0 ml/hr. If the turn screw 40 is now loosened, by rotation about axis AR, so as to pull plate 184 upwardly, cam 186 will bear against and deflect tube 188. This restricts passage of fluid flow, with the adjustment, over 180° of rotation, varying the capillary flow rate from 3.0 ml/hr to 30 ml/hr.

When the push button 42 is depressed axially downward against the force of spring 194, the cam 186 is displaced downwardly to free the tube, permitting unrestricted flow of fluid therethrough for maximum capillary flow rate on the order of 30 ml/hr. This provides an override or bypass function. Turn screw 40 is limited in its rotation by stop pin 196 extending upwardly from flange 140 and which, during operation, rides in an arcuate groove 198 in the underside of the rotatable flange portion 200 of the turn screw 40. This arcuate groove 198 extends for 180°, which defines the limits of rotation of the turn screw for adjusting capillary flow rate.

The capillary tube 188 extends through the opening between support rods 180 and 182. The opposite ends of the capillary tube are mounted for fluid flow with apertures 202 and 204 in the valve body 130. Aperture 202 is vertically spaced upward from opening 158. Similarly, aperture 204 is spaced vertically upward from opening 166 in the valve body.

Figure 8:
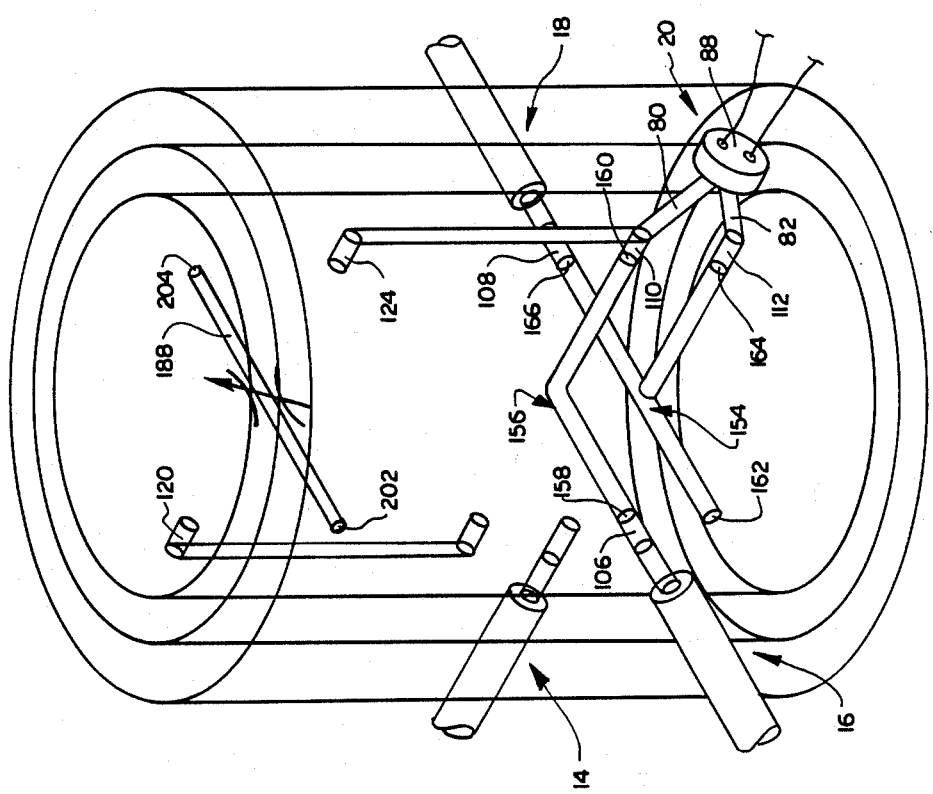
FIG. 8 is a schematic illustration of the valve operation during flush operations.
Figure 9:
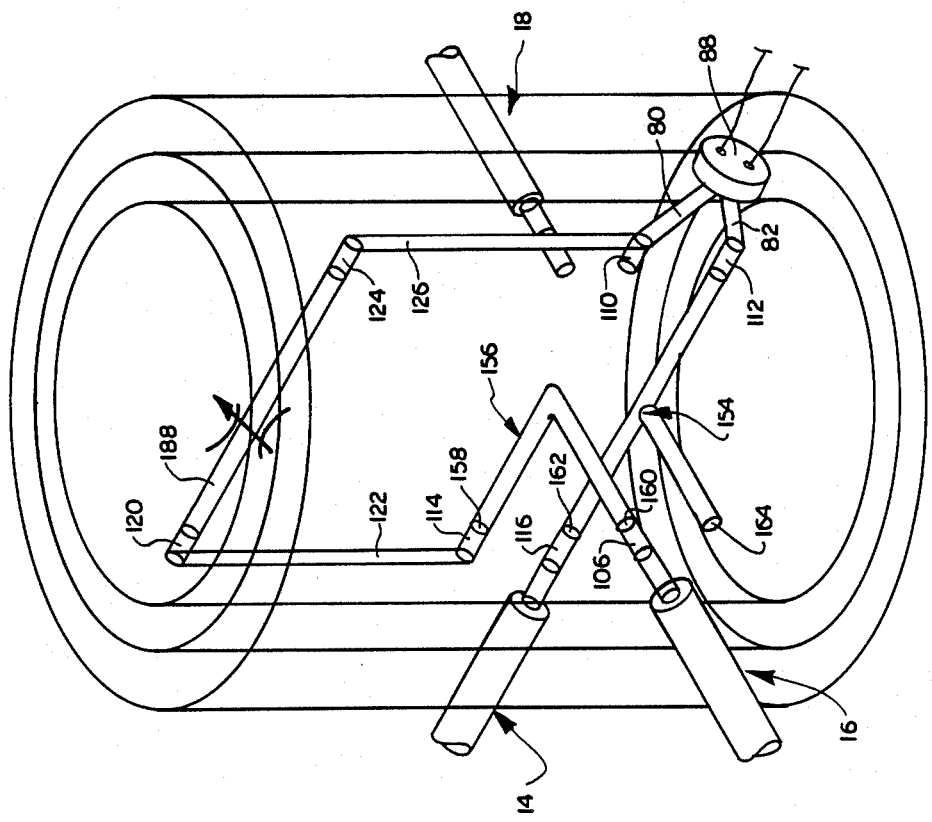
FIG. 9 is a schematic illustration of the valve operation during pressure monitoring operations.

Reference is now made to FIGS. 8, 9 and 10 which schematically illustrate the operation of the fluid control device in the valve actuator positions A, B and C. FIG. 8 illustrates position A or the flush position. In this position, it is seen that the capillary tube 188 is blocked from fluid flow since apertures 202 and 204 in the valve body 130 are not in alignment with apertures 120 and 124 in the valve sleeve 104. Also, the patient port 14 is blocked in this position of the valve body. Thus, the upper or L-shaped passage way 156 has its opening 158 in registry with aperture 106 in the valve sleeve 104 and this leads to the parenteral fluid port 16. The opening 160 of passageway 156 is in registry with aperture 110 in the valve sleeve 104 and this leads to the pressure chamber 20 by way of aperture 80. Also in this position of the valve body, the T-shaped passageway 154 is positioned so that its opening 162 is blocked and its opening 166 is in registry with aperture 108 in the valve sleeve 104 and this leads to the patient port 18. Also in this position, opening 164 of the passageway 154 is in registry with aperture 112 in the valve sleeve 104 and this leads to the pressure chamber by way of aperture 82. Consequently, in this position fluid flow is had from the parenteral supply 36 into the housing by way of port 16 through passageway 156 in the valve body, and through the pressure transducer back into the valve body within passageway 154 and exits from the valve body through the sample port 18. This position of the rotary actuator 60 permits flushing of the system to eliminate trapped air bubbles and is the initial connection during operation.

The operator may now rotate the valve actuator 60 in a clockwise direction about axis AR as viewed in FIG. 1 from position A to position B. This may be the most commonly utilized position from a clinical setting to provide continuous dynamic pressure measurements. In this position as depicted in FIG. 9, the capillary tube 188 is aligned with apertures 120 and 124 in the valve sleeve 104 for fluid flow therebetween. The sampling port 18 is blocked in this position of the valve body. The L-shaped passageway 156 has its opening 160 in registry with aperture 106 in the valve sleeve 104 for fluid communication with the parenteral port 16. The other opening 158 of passageway 156 is in alignment with aperture 114 in the valve sleeve 104 permitting parenteral flow communication through the valve body and upwardly along groove 122 and through the capillary tube 188 and thence downwardly through groove 126 to the flow-through pressure sensor 88. Also in this position, the T-shaped passageway 154 is located such that its opening 164 is blocked while opening 162 is in registry with aperture 116 in the valve sleeve leading to the patient port 14. Additionally, opening 166 of passageway 154 is in registry with aperture 112 in the valve sleeve and by completing that for the parenteral fluid flow through the flow-through pressure sensor 88 and thence through the passageway 154 through the patient port 14. Parenteral fluid may flow through the valve body by way of the capillary tube thence exiting from the patient port 14 to the patient to thereby maintain patency. The capillary flow rate is adjustable by rotating the capillary turn screw 40 so that the flow rate may be adjusted from 3.0 ml/hr to 30 ml/hr to accommodate various patient needs. The adjusted flow rate may be bypassed by the operator depressing push button 42 to remove the restriction imposed on the capillary tube to permit the upper flow rate, i.e., the 30 ml/hr. In this position, the blood pressure is transmitted by way of the parenteral fluid through the flow-through pressure sensor 88 and the operator may obtain a reading by monitoring the pressure meter 52.

The operator may now rotate the valve actuator 60 counterclockwise 180° about the axis of rotation AR from position B to position C. In this position as depicted in FIG. 10, the parenteral fluid port 16 is blocked and the only fluid passageway through the valve body is from the patient by way of the patient port 14, through aperture 116 in the valve sleeve 104, into the lower T-shaped passageway 154 within the valve body by way of its opening 166, through the passageway and out through its opening 164 and then exit through aperture 108 in the valve sleeve 104 and through the sampling port 18. Blood may be sampled as by a syringe 50 or the like. In this position, blood can be returned from the sample syringe to the patient and the system can be flushed.

Whereas the invention has been described in conjunction with a preferred embodiment, it is to be appreciated that various modifications and arrangements may be made without departing from the spirit and scope of the invention as defined by the appended claims.

Having described specific preferred embodiments of the invention, the following is claimed:

1. Apparatus for use in externally monitoring parameters of blood and for obtaining blood samples from a single communication access to a patient's blood vessel, comprising:
   a housing having a sample port for fluid communication with blood sampling means, a patient port for fluid communication with a patient's blood vessel by way of said single communication access, a parenteral port for fluid communication with a pressurized source of parenteral fluid and a flow through pressure chamber having first and second inlet-outlet passageways permitting fluid flow through said chamber and having a pressure sensor therein positioned relative to said passageways to be responsive to the pressure of fluid flowing through said chamber;

flow control means for selectively controlling the fluid flow between said ports and said pressure chamber, said control means having a first condition completing a fluid flow path from said parenteral port through said pressure chamber to said patient port while blocking said sample port so that the parenteral fluid will be in fluid communication with the patient's blood for monitoring blood pressure transmitted by said parenteral fluid and maintaining patency of said access, a second condition completing a fluid flow path from said parenteral port through said pressure chamber to said sample port while blocking said patient port for flushing the flow path and minimizing production of air bubbles, and a third condition completing a fluid flow path from said patient port to said sample port while blocking said parenteral port for sampling blood.

2. Apparatus as set forth in claim 1 wherein said flow control means includes a valve body movably mounted within said housing for movement therein and a valve actuator drivingly connected to said valve body for selectively displacing said valve body to first, second and third positions within said housing wherein said positions respectively correspond with said first, second and third conditions of said flow control means.

3. Apparatus as set forth in claim 2 wherein said valve body is mounted for rotation within said housing about an axis of rotation and wherein said valve actuator operates to rotatably drive said valve body about said axis of rotation.

4. Apparatus as set forth in claim 3 wherein said valve body is an elongated member coaxially surrounding said axis of rotation and having a plurality of fluid flow passageways extending radially therethrough, said housing having an interior wall defining said opening for receiving said valve body for rotation therein, said wall having apertures extending radially therethrough with a first aperture extending to said patient port, a second aperture extending to said parenteral port, and a third aperture extending to said sampling port, said plurality of passageways through said valve body adapted to be in registry with various of said apertures depending upon the rotational position of said valve body within said housing.

5. Apparatus as set forth in claim 4 wherein said housing has fourth and fifth apertures respectively communicating with said first and second inlet-outlet passageways leading to said pressure chamber for completing a path for fluid flow past said pressure sensor.

6. Apparatus as set forth in claim 5 wherein said plurality of passageways in said valve body include a first and second passageway for completing fluid flow paths through said valve body between said apertures in said housing depending upon the rotational position of said valve body.

7. Apparatus as set forth in claim 5 including a capillary flow tube carried by said valve body and adapted to complete a fluid flow path from said parenteral port to said pressure chamber when said valve body is in said first position.

8. Apparatus for use in externally monitoring parameters of blood and for obtaining blood samples from a single communication access to a patient's blood vessel, comprising:

a housing having a sample port for fluid communication with blood sampling means, a patient port for fluid communication with a patient's blood vessel by way of said single communicatin access, a parenteral port for fluid communication with a pressurized source of parenteral fluid and a pressure chamber having a pressure sensor therein responsive to the pressure of fluid flowing through said chamber;

flow control means for selectively controlling the fluid flow between said ports and said pressure chamber, said control means having a first condition completing a fluid flow path from said parenteral port through said pressure chamber to said patient port while blocking said sample port for monitoring blood pressure and maintaining patency of said access, a second condition completing a fluid flow path from said parenteral port to said sample port while blocking said patient port for flushing the flow path and minimizing production of air bubbles, and a third condition completing a fluid flow path from said patient port to said sample port while blocking said parenteral port for sampling blood;

said flow control means includes a valve body movably mounted within said housing for movement therein and a valve actuator drivingly connected to said velve body for selectively displacing said valve body to first, second and third positions within said housing wherein said positions respectively correspond with said first, second and third conditions of said flow control means;

said valve body is mounted for rotation within said housing about an axis of rotation and wherein said valve actuator operates to rotatably drive said valve body about said axis of rotation;

said valve body is an elongated member coaxially surrounding said axis of rotation and having a plurality of fluid flow passageways extending radially therethrough, said housing having an interior wall defining said opening for receiving said valve body for rotation therein, said wall having apertures extending radially therethrough with a first aperture extending to said patient port, a second aperture extending to said parenteral port, and a third aperture extending to said sampling port, said plurality of passageways through said valve body adapted to be in registry with various of said apertures depending upon the rotational position of said valve body within said housing;

said housing has fourth and fifth apertures leading to said pressure chamber for completing a path for fluid flow past said pressure sensor;

a capillary flow tube carried by said valve body and adapted to complete a fluid flow path from said parenteral port to said pressure chamber when said valve body is in said first position; and capillary flow adjusting means associated with said capillary tue for varying the rate of flow of fluid therethrough.

9. Apparatus as set forth in claim 8 wherein said capillary tube is resilient and said adjusting means includes means for engaging and deflecting said tube to restrict fluid flow therethrough.

10. Apparatus as set forth in claim 9 wherein said adjusting means includes a turn screw carried by said rotary valve actuator and cam means associated with said turn screw for engaging and deflecting said tube to restrict fluid flow therethrough.

11. Apparatus as set forth in claim 10 including capillary adjusting bypass means for disengaging said cam means from said tube to permit unrestricted fluid flow through said capillary tube.

12. Apparatus as set forth in claim 11 wherein said bypass means includes a push button carried by said turn screw and operatively associated with said cam means for, when said button is depressed, causing said cam means to become disengaged from said tube.

13. Apparatus as set forth in claim 8 wherein said patient port includes a sensing chamber containing an inlet passageway for fluid flow therethrough, at least one blood parameter sensor carried by said chamber and positioned for sensing a blood related parameter when blood flows through said inlet passageway from a said patient into said patient port during blood sampling operation.

14. Apparatus as set forth in claim 13 including a plurality of blood parameter sensors for sensing a plurality of blood related parameters as blood flows from said patient into said patient port.

15. Apparatus as set forth in claim 13 wherein said fluid control means includes means movably mounted in said housing for selectively completing said flow paths when positioned in first, second and third positions therein and wherein said positions respectively correspond with said first, second and third conditions of said fluid control means, and a single valve actuator drivingly coupled to said valve means for selectively positioning said valve means to one of said positions.

16. Apparatus as set forth in claim 15 including capillary flow means carried by said valve means for movement therewith and adapted, when said valve means is in its first position, to be in the fluid flow path from said parenteral port to said patient port.

17. Apparatus as set forth in claim 16 wherein said capillary means is adjustable to control the capillary flow rate of parenteral fluid therethrough for maintaining patency of said access.

* * * * *